US008106245B2

(12) United States Patent
Krafft et al.

(10) Patent No.: US 8,106,245 B2
(45) Date of Patent: Jan. 31, 2012

(54) METHOD FOR PREPARING CHLOROHYDRIN BY CONVERTING POLYHYDROXYLATED ALIPHATIC HYDROCARBONS

(75) Inventors: Philippe Krafft, Rhode Saint Genese (BE); Patrick Gilbeau, Braine-le-Comte (BE)

(73) Assignee: Solvay (Société Anonyme), Brussels (BE)

( * ) Notice: Subject to any disclaimer, the term of this patent is extended or adjusted under 35 U.S.C. 154(b) by 713 days.

(21) Appl. No.: 11/914,891

(22) PCT Filed: May 19, 2006

(86) PCT No.: PCT/EP2006/062461
§ 371 (c)(1),
(2), (4) Date: Nov. 19, 2007

(87) PCT Pub. No.: WO2006/100319
PCT Pub. Date: Sep. 28, 2006

(65) Prior Publication Data
US 2008/0194847 A1    Aug. 14, 2008

Related U.S. Application Data

(60) Provisional application No. 60/734,635, filed on Nov. 8, 2005, provisional application No. 60/734,657, filed on Nov. 8, 2005, provisional application No. 60/734,636, filed on Nov. 8, 2005, provisional application No. 60/734,627, filed on Nov. 8, 2005, provisional application No. 60/734,634, filed on Nov. 8, 2005, provisional application No. 60/734,658, filed on Nov. 8, 2005, provisional application No. 60/734,637, filed on Nov. 8, 2005, provisional application No. 60/734,659, filed on Nov. 8, 2005.

(30) Foreign Application Priority Data

May 20, 2005  (EP) ..................... 05104321
May 20, 2005  (FR) ..................... 05 05120

(51) Int. Cl.
C07C 31/34    (2006.01)
C07D 301/02   (2006.01)
C08G 59/00    (2006.01)
(52) U.S. Cl. ......... 568/841; 568/844; 549/518; 528/405
(58) Field of Classification Search .................. 568/841, 568/844; 549/518; 528/405
See application file for complete search history.

(56) References Cited

U.S. PATENT DOCUMENTS

| 280,893 A | 7/1883 | Baujard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Hermann |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,255,470 A | 3/1981 | Cohen et al. |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,595,469 A | 6/1986 | Foller |

(Continued)

FOREIGN PATENT DOCUMENTS

CA    1119320    8/2003

(Continued)

OTHER PUBLICATIONS

U.S. Appl. No. 11/914,879, filed Nov. 19, 2007, Gilbeau.

(Continued)

*Primary Examiner* — Taylor Victor Oh
(74) *Attorney, Agent, or Firm* — Oblon, Spivak, McClelland, Maier & Neustadt, L.L.P.

(57) ABSTRACT

Process for preparing a chlorohydrin, wherein a polyhydroxylated aliphatic hydrocarbon whose total metal content, expressed in elemental form, is greater than or equal to 0.1 µg/kg and less than or equal to 1000 mg/kg is reacted with a chlorinating agent.

19 Claims, No Drawings

U.S. PATENT DOCUMENTS

| | | | |
|---|---|---|---|
| 4,609,751 A | 9/1986 | Hajjar | |
| 4,634,784 A | 1/1987 | Nagato et al. | |
| 4,655,879 A | 4/1987 | Brockmann et al. | |
| 4,935,220 A | 6/1990 | Schneider et al. | |
| 4,960,953 A | 10/1990 | Jakobson et al. | |
| 4,973,763 A | 11/1990 | Jakobson et al. | |
| 4,990,695 A | 2/1991 | Buenemann et al. | |
| 5,041,688 A | 8/1991 | Jakobson et al. | |
| 5,200,163 A | 4/1993 | Henkelmann et al. | |
| 5,278,260 A | 1/1994 | Schaffner et al. | |
| 5,286,354 A | 2/1994 | Bard et al. | |
| 5,344,945 A | 9/1994 | Grunchard | |
| 5,359,094 A | 10/1994 | Teles et al. | |
| 5,393,428 A | 2/1995 | Dilla et al. | |
| 5,445,741 A | 8/1995 | Dilla et al. | |
| 5,478,472 A | 12/1995 | Dilla et al. | |
| 5,567,359 A | 10/1996 | Cassidy et al. | |
| 5,578,740 A | 11/1996 | Au et al. | |
| 5,710,350 A | 1/1998 | Jeromin et al. | |
| 5,731,476 A | 3/1998 | Shawl et al. | |
| 5,744,655 A | 4/1998 | Thomas et al. | |
| 5,779,915 A | 7/1998 | Becker et al. | |
| 5,908,946 A | 6/1999 | Stern et al. | |
| 5,993,974 A | 11/1999 | Fukushima et al. | |
| 6,142,458 A | 11/2000 | Howk | |
| 6,177,599 B1 | 1/2001 | Cowfer et al. | |
| 6,270,682 B1 | 8/2001 | Santen et al. | |
| 6,288,248 B1 | 9/2001 | Strebelle et al. | |
| 6,288,287 B2 | 9/2001 | Ueoka et al. | |
| 6,350,888 B1 | 2/2002 | Strebelle et al. | |
| 6,350,922 B1 | 2/2002 | Vosejpka et al. | |
| 6,719,957 B2 | 4/2004 | Brady, Jr. et al. | |
| 6,740,633 B2 | 5/2004 | Norenberg et al. | |
| 7,126,032 B1 | 10/2006 | Aiken | |
| 7,128,890 B2 | 10/2006 | Ollivier | |
| 7,473,809 B2 * | 1/2009 | Kubicek et al. | 568/841 |
| 7,584,629 B2 | 9/2009 | Sohn et al. | |
| 2001/0014763 A1 | 8/2001 | Ueoka et al. | |
| 2003/0209490 A1 | 11/2003 | Camp et al. | |
| 2004/0016411 A1 | 1/2004 | Joyce et al. | |
| 2004/0024244 A1 | 2/2004 | Walsdorff et al. | |
| 2004/0150123 A1 | 8/2004 | Strofer et al. | |
| 2004/0179987 A1 | 9/2004 | Oku et al. | |
| 2004/0232007 A1 | 11/2004 | Carson et al. | |
| 2005/0261509 A1 | 11/2005 | Delfort et al. | |
| 2006/0052272 A1 | 3/2006 | Meli et al. | |
| 2006/0079433 A1 | 4/2006 | Hecht et al. | |
| 2006/0123842 A1 | 6/2006 | Sohn et al. | |
| 2007/0112224 A1 | 5/2007 | Krafft et al. | |
| 2007/0293707 A1 | 12/2007 | Wolfert et al. | |
| 2008/0146753 A1 | 6/2008 | Woike et al. | |
| 2008/0154050 A1 | 6/2008 | Gilbeau | |
| 2008/0281132 A1 | 11/2008 | Krafft et al. | |
| 2009/0022653 A1 | 1/2009 | Strebelle et al. | |
| 2009/0198041 A1 | 8/2009 | Krafft et al. | |
| 2010/0029959 A1 | 2/2010 | Fan et al. | |

FOREIGN PATENT DOCUMENTS

| | | |
|---|---|---|
| CN | 1296003 A | 5/2001 |
| CN | 10141421 | 9/2007 |
| DE | 58396 | 8/1891 |
| DE | 180 668 | 1/1906 |
| DE | 197 308 | 11/1906 |
| DE | 238 341 | 3/1908 |
| DE | 869 193 | 3/1953 |
| DE | 1 041 488 | 10/1958 |
| DE | 1 075 103 | 2/1960 |
| DE | 1 226 554 | 10/1966 |
| DE | 2 241 393 | 2/1974 |
| DE | 25 21 813 | 12/1975 |
| DE | 30 03 819 | 8/1981 |
| DE | 216 471 | 6/1983 |
| DE | 32 43 617 | 5/1984 |
| DE | 37 21 003 | 6/1987 |
| DE | 43 02 306 | 8/1994 |
| DE | 102 03 914 | 1/2002 |
| DE | 102 54 709 | 6/2004 |
| DE | 238341 | 3/2008 |
| DE | 197 309 | 4/2008 |
| EP | 0 296 341 | 12/1988 |
| EP | 0 347 618 | 12/1989 |
| EP | 0 421 379 | 4/1991 |
| EP | 0 452 265 | 10/1991 |
| EP | 0 518 765 | 12/1992 |
| EP | 0 522 382 | 1/1993 |
| EP | 0 535 949 | 4/1993 |
| EP | 0 563 720 | 10/1993 |
| EP | 0 568 389 | 11/1993 |
| EP | 0 582 201 | 2/1994 |
| EP | 0 618 170 | 10/1994 |
| EP | 0 916 624 | 5/1999 |
| EP | 0 919 551 | 6/1999 |
| EP | 0 774 450 | 2/2000 |
| EP | 1 059 278 | 12/2000 |
| EP | 1 106 237 | 6/2001 |
| EP | 1 153 887 | 11/2001 |
| EP | 1 163 946 | 12/2001 |
| EP | 1 298 154 | 4/2003 |
| EP | 0 561 441 | 9/2003 |
| EP | 1 411 027 | 4/2004 |
| EP | 1 752 435 | 2/2007 |
| EP | 1 752 436 | 2/2007 |
| EP | 1 760 060 | 3/2007 |
| EP | 1 762 556 | 3/2007 |
| EP | 1 770 081 | 4/2007 |
| EP | 1 772 446 | 4/2007 |
| EP | 1 775 278 | 4/2007 |
| EP | 2 085 364 | 8/2009 |
| FR | 1 306 231 | 10/1961 |
| FR | 1 417 388 | 10/1964 |
| FR | 1 476 073 | 4/1966 |
| FR | 1 577 792 | 8/1968 |
| FR | 2 180 138 | 5/1973 |
| FR | 2 217 372 | 2/1974 |
| FR | 2 565 229 | 12/1985 |
| FR | 2 752 242 | 2/1998 |
| FR | 2 862 644 | 5/2005 |
| FR | 2 868 419 | 10/2005 |
| FR | 2 869 612 | 11/2005 |
| FR | 2 869 613 | 11/2005 |
| FR | 2 872 504 | 1/2006 |
| FR | 2 881 732 | 8/2006 |
| FR | 2 885 903 | 11/2006 |
| FR | 2 912 743 | 8/2008 |
| FR | 2 913 683 | 9/2008 |
| FR | 2 917 411 | 12/2008 |
| FR | 2 918 058 | 1/2009 |
| FR | 2 925 045 | 6/2009 |
| FR | 2 929 611 | 10/2009 |
| FR | 2 935 699 | 3/2010 |
| FR | 2 935 968 | 3/2010 |
| GB | 14 767 | 0/1914 |
| GB | 404 938 | 7/1932 |
| GB | 406345 | 8/1932 |
| GB | 467 481 | 9/1935 |
| GB | 541357 | 11/1941 |
| GB | 679 536 | 9/1952 |
| GB | 736641 | 7/1953 |
| GB | 799 567 | 8/1958 |
| GB | 1083594 | 11/1964 |
| GB | 984446 | 2/1965 |
| GB | 984 633 | 3/1965 |
| GB | 1 387 668 | 3/1972 |
| GB | 1286893 | 8/1972 |
| GB | 1 493 538 | 4/1975 |
| GB | 1 414 976 | 11/1975 |
| GB | 2 173 496 | 10/1986 |
| GB | 702143 | 10/1990 |
| GB | 2 336 584 | 10/1999 |
| HU | 2002-003023 | 3/2004 |
| JP | 39-27230 | 11/1928 |
| JP | 50-062909 | 5/1975 |
| JP | 55-041858 | 3/1980 |
| JP | 56-29572 | 3/1981 |
| JP | 56-99432 | 8/1981 |
| JP | 61-112066 | 5/1986 |

| | | |
|---|---|---|
| JP | 62-242638 | 10/1987 |
| JP | 63-195288 | 8/1988 |
| JP | 2-137704 | 5/1990 |
| JP | 03-014527 | 1/1991 |
| JP | 3-223267 | 10/1991 |
| JP | 03-223267 | 10/1991 |
| JP | 04-089440 | 3/1992 |
| JP | 04-217637 | 8/1992 |
| JP | 6-25196 | 4/1994 |
| JP | 6-184024 | 7/1994 |
| JP | 06-321852 | 11/1994 |
| JP | 8-59593 | 3/1996 |
| JP | 09-299953 | 11/1997 |
| JP | 10-139700 | 5/1998 |
| JP | 10-218810 | 8/1998 |
| JP | 2001-037469 | 2/2001 |
| JP | 2001-213827 | 8/2001 |
| JP | 2001-261308 | 9/2001 |
| JP | 2001-1261581 | 9/2001 |
| JP | 2002-02033 | 1/2002 |
| JP | 2002-038195 | 2/2002 |
| JP | 2002-363153 | 12/2002 |
| JP | 2003-81891 | 3/2003 |
| JP | 2003-89680 | 3/2003 |
| JP | 2005-007841 | 1/2005 |
| JP | 2005-097177 | 4/2005 |
| JP | 76021635 | 4/2005 |
| JP | 2007-008898 | 1/2007 |
| JP | 2009-263338 | 11/2009 |
| KR | 900006513 | 11/1987 |
| KR | 2003-29740 | 5/2003 |
| KR | 10-0514819 | 11/2004 |
| SU | 123153 | 1/1959 |
| SU | 1125226 | 11/1984 |
| SU | 1159716 | 6/1985 |
| SU | 1685969 | 10/1991 |
| WO | WO 95/14639 | 6/1995 |
| WO | WO 96/07617 | 3/1996 |
| WO | WO 96/15980 | 5/1996 |
| WO | WO 97/48667 | 12/1997 |
| WO | WO 98/37024 | 8/1998 |
| WO | WO 99/14208 | 3/1999 |
| WO | WO 99/32397 | 7/1999 |
| WO | WO 01/86220 | 11/2001 |
| WO | WO 02/26672 | 4/2002 |
| WO | WO 03/064357 | 8/2003 |
| WO | WO 2004/056758 | 7/2004 |
| WO | WO 2005/021476 | 3/2005 |
| WO | WO 2005/054167 | 6/2005 |
| WO | WO 2005/097722 | 10/2005 |
| WO | WO 2005/115954 | 12/2005 |
| WO | WO 2005/116004 | 12/2005 |
| WO | WO 2006/020234 | 2/2006 |
| WO | WO 2006/100311 | 9/2006 |
| WO | WO 2006/100312 | 9/2006 |
| WO | WO 2006/100313 | 9/2006 |
| WO | WO 2006/100314 | 9/2006 |
| WO | WO 2006/100315 | 9/2006 |
| WO | WO 2006/100316 | 9/2006 |
| WO | WO 2006/100317 | 9/2006 |
| WO | WO 2006/100318 | 9/2006 |
| WO | WO 2006/100319 | 9/2006 |
| WO | WO 2006/100320 | 9/2006 |
| WO | WO 2006/106153 | 10/2006 |
| WO | WO 2006/106154 | 10/2006 |
| WO | WO 2006/106155 | 10/2006 |
| WO | WO 2007/005405 | 5/2007 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

U.S. Appl. No. 11/915,059, filed Nov. 20, 2007, Gilbeau et al.
U.S. Appl. No. 11/914,836, filed Nov. 19, 2007, Krafft et al.
U.S. Appl. No. 11/915,067, filed Nov. 20, 2007, Krafft et al.
U.S. Appl. No. 11/914,874, filed Nov. 19, 2007, Krafft et al.
U.S. Appl. No. 11/914,862, filed Nov. 19, 2007, Gilbeau.
U.S. Appl. No. 11/914,856, filed Nov. 19, 2007, Krafft et al.
U.S. Appl. No. 11/914,868, filed Nov. 19, 2007, Krafft.
U.S. Appl. No. 11/915,046, filed Nov. 20, 2007, Krafft et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft et al.
U.S. Appl. No. 60/560,676, filed Apr. 8, 2004.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 60/734,636, filed Nov. 8, 2005.
U.S. Appl. No. 61/013,680, filed Dec. 14, 2007, Krafft et al.
U.S. Appl. No. 61/013,704, filed Dec. 14, 2007, Gilbeau et al.
U.S. Appl. No. 61/013,676, filed Dec. 14, 2007, Borremans.
U.S. Appl. No. 61/013,707, filed Dec. 14, 2007, Krafft et al.
U.S. Appl. No. 61/013,672, filed Dec. 14, 2007, Krafft et al.
U.S. Appl. No. 61/013,713, filed Dec. 14, 2007, Gilbeau.
U.S. Appl. No. 61/013,710, filed Dec. 14, 2007, Krafft et al.
U.S. Appl. No. 61/007,661, filed Dec. 14, 2007.
Semendyava, N. D. et al., Khimicheskaya Promyshlennost, Seriya: Khornaya Promyshlennost (1981), 5, 21-2 (CA Summary) XP 002465275.
Rudnenko, E.V., et al., Kakokrasochnye Materialy I Ikh Primenenie (1988), 4, 69-71 (CA Summary) XP 002465276.
Kirk Othmer Encyclopedia of Chemical Technology, Third Edition, vol. 12, 1980, pp. 1002-1005.
Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Product Brouchure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Herman A. Bruson, et al., "Thermal Decomposition of Glyceryl Carbonates," Journal of the American Chemical Society, vol. 74, Apr. 1952 pp. 2100-2101.
Catalogue of Nittetu Chemical Engineering Ltd. (Published in Mar. 1994).
12093 Chemicals, Chemical Daily Co., Ltd. (Published on Jan. 22, 1993) with attached English translation of relevant excerpts.
Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd.
Perry's Chemical Engineers Handbook $7^{th}$ Ed. $11^{th}$ Section, 1997.
Perry's Chemical Engineers Handbook $7^{th}$ Ed. $13^{th}$ Section, 1997.
Perry's Chemical Engineers Handbook $7^{th}$ Ed. $15^{th}$ Section, 1997.
Ullmann Encyclopedia Industr. Chem. $5^{th}$ Ed., vol. A23, 1993 pp. 635-636.
Ullmann Encyclopedia Industr. Chem. $5^{th}$ Ed., vol. A13, 1989 pp. 289.

Ullmann Encyclopedia Industr. Chem. 5$^{th}$ Ed., vol. A11, 1988 pp. 354-360.
U.S. Appl. No. 12/304,391, filed Dec. 11, 2008, Krafft et al.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte—und Wassermengenwirtschaft e; V; - 2005 p. 81/- 8/5., vol. 5.
Klaus Weissermel, et al., "Industrial Organic Chemistry," (3$^{rd}$ Completely Revised Edition); VCH 1997. p. 93-98.
Klaus Weissermel, et al., "Industrial Organic Chemistry," (3$^{rd}$ Completely Revised Edition); VCH 1997. p. 276-277.
Klaus Weissermel, et al., "Industrial Organic Chemistry," (3$^{rd}$ Completely Revised Edition); VCH 1997. p. 347-355.
U.S. Appl. No. 12/502,296, filed Jul. 14, 2009, Krafft et al.
U.S. Appl. No. 12/502,342, filed Jul. 14, 2009, Krafft et al.
U.S. Appl. No. 12/527,538, filed Aug. 17, 2009, Gilbeau et al.
U.S. Appl. No. 12/529,777, filed Sep. 3, 2009, Krafft et al.
U.S. Appl. No. 12/529,778, filed Sep. 3, 2009, Krafft et al.
M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.
U.S. Appl. No. 12/600,018, filed Nov. 13, 2009, Borremans et al.
U.S. Appl. No. 12/663,753, filed Dec. 9, 2009, Krafft et al.
U.S. Appl. No. 12/663,744, filed Dec. 9, 2009, Boulos et al.
U.S. Appl. No. 12/663,749, filed Dec. 9, 2009, Krafft et al.
U.S. Appl. No. 12/663,887, filed Dec. 10, 2009, Kraftt et al.
U.S. Appl. No. 12/681,083, filed Mar. 31, 2010, Bobet et al.
RD 436093, Aug. 10, 2000, Research Disclosure.
Ullman's Encyclopedia of Industrial Chemistry, 2005, Wiley-VCH GmbH & Co., KgaA, Weinhem, pp. 8-15 and 401-477, Published online Mar. 15, 2001.
U.S. Appl. No. 12/864,211, filed Jul. 27, 2010, Gilbeau et al.
Production and Prospect of the World Natural Glycerol by Zhu Shiyong, Cereals and Oils, vol. 1, 1997, pp. 33-38 (No English Translation).
Vinnolit; Vinnolit receives EU grant for water recycling project; Press Release, 2008: http://www.vinnolit.de/vinnolit.nsf/id/EN_Vinnolit_receives_EU_grant_for_water_recycling_project_.
N.W. Zieis, Journal of American Oil Chemists' Society, Nov. 1956, vol. 33, pp. 556-565.
U.S. Appl. No. 13/060,421, filed Feb. 23, 2011, Balthasart et al.
Perry's Chemical Engineers Handbook, Sixth Edition, McGraw-Hill Inc., (1984) Section 18.
Vol. B3; Unit Operations II of Ullmann's Encyclopedia of Industrial Chemistry, Fifth Completely Revised Edition, Published by VCH, 1988.
U.S. Appl. No. 13/051,007, filed Mar. 18, 2011, Krafft et al.
U.S. Appl. No. 13/063,230, filed Mar. 10, 2011, Krafft et al.
Ma Zengxin, Gan Yicui, Recovery of Polyglycerol from Residues of Synthetic Glycerol—Riyong Huaxue Gongye, 1997, 4, 21023 (Abstract Only).
U.S. Appl. No. 12/935,538, filed Sep. 29, 2010, Gilbeau et al.
Gibson., "The Preparation, Properties, and Uses of Glycerol Derivatives. Part III. The Chlorohydrins", Chemistry and Industry, Chemical Society, pp. 949-975, 1931.
Carre et al., "La Transformation Des Alcools Polyatomiques en Mono-Et En Polychlorhydrines Au Moyen Du Chlorure De Thionyle", Bull. Soc. Chim. Fr., No. 49, pp. 1150-1154, 1931.
Fauconnier, "Preparation De L'Epichlorhydrine", Bull. Soc. Chim. Fr., No. 50, pp. 212-214, 1888.
"Industrially Important Epoxides", Ullmann's Encyclopedia of Industrial Chemistry, 5.ed, vol. A9, pp. 539-540, 1987.
Bonner et al., "The Composition of Constant Boiling Hydrochloric Acid at Pressures of 50 to 1220 millimeters", Journal of American Chemical Society, vol. 52, pp. 633-635, 1930.
Muskopf et al., "Epoxy Resins", Ullmann's Encyclopedia of Industrial Chemistry, 5.ed, vol. A9, pp. 547-562, 1987.
Armando Novelli, "The Preparation of Moni- and Dichlorohydrins of Glycerol," Anal. Farm. Bioquim, vol. 1, 1930, pp. 8-19 (with English Abstract).
Derwent Publications, AN 109:6092 CA, JP 62-242638 (Oct. 23, 1987).
Derwent Publications, AN 1987-338139 [48], JP 62-242638, (Oct. 23, 1987).
Kirk-Othmer Encyclopedia of Chemical Technology, Third Edition, vol. 4, Blood, Coagulants and Anticoagulants to Cardiovascular Agents, 1978.
J.B. Conant et al., "Glycerol a,y-Dichlorophydrin," Organic Syntheses Coll., vol. 1, p. 292, 1941.
I. Miyakawa et al., Nagoya Sangyo Kagaku Kenkyusho Kenkyu Hokoku, 10, 49-52 (1957).
Han Xiu-Ying et al., Shanxi Daxue Xueba Bianjibu, 2002, 25(4), 379-80).
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870, 1999.
Oleoline, com, Glycerine Market report, Sep. 10, 2003, No. 62.
Notification Under Act No. 100/2001, Coll. As Amended by Act No. 93/2004, Coll. to the extent of Annex No. 4 (Spolek) Nov. 30, 2004.
Documentation Under Act No. 100/2001 Coll. As amended by Act. No. 93/2004 Coll in the scope of appendix No. 4 (Spolek) Jan. 11, 2005.
K. Weissermel and H J. Arpe in Industrial Organic Chemistry, Third, Completely Revised Edition, VCH, 1997, pp. 149, 275.
Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition, 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429, 1985.
Ullmann's Encyclopedia of Industrial Chemistry, Fifth Completely REvised Edition, vol. A6, pp. 240-252, 1986.
Hancock, E.G., Propylene and its Industrial Derivatives, 1973, pp. 298-332.
K. Weissermel and H. J. Arpe in Industrial Organic Chemistry, Third, Completely Revised Edition, VCH 1997, pp. 149-163.
K. Weissermel and H. J. Arpe in Industrial Organic Chemistry, Third, Completely Revised Edition, VCH 1997, pp. 275-276.
Ullmann's Encylcopedia of Industrial Chemistry, Fifth Completely Revised Edition, vol. A9, pp. 539-540, 1987.
Perry's Chemical Engineers Handbook, Sixth Edition, Robert H. Perry, Don Green, 1984, Section 21-44 to 21-68.
Iwanami Dictionary of Physics and Chemistry, Third edition, Ryo Midorikawa/Iwanami Shoten, Publishers, May 29, 1971, pp. 270-271, 595 and 726.
Expert Opinion on the Environment Impact Assessment Documentation Pursuant to Annex No. 5 of Act. No. 100/2001 Coll., as amended by later regulation of the project/intent combined process for the manufacture of epichlorohydrin (Spolek) Apr. 2005.
Fauconnier, "Preparation of Epichlorohydrin," Bull. Soc. Chim. Fr., No. 122, pp. 212-214 (With English Translation), 1884.
U.S. Appl. No. 12/745,802, filed Jun. 2, 2010, Gilbeau et al.
Medium and Long-Term Opportunities and Risks of the Biotechnologial Production of Bulk Chemicals from Renewable Resources—The Potential of White Biotechnology—the BREW Project—Final Report—Prepared under the European Commission's GRXTH Programme (DG Research) Utrecht, Sep. 2006 (pp. 29-31).
Ullmann Encly. Industr. Chem., 5$^{th}$ Ed., vol. A6, (1988), pp. 401-477.
Polymer Science Dictionary, M.S.M., Elsevier Applied Chemistry, London and New York 1989, p. 86.
Perry's chemical Engineers' Handbook, Sixth Edition, Section 21, pp. 21-55, 1984.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

Myszkowski J. et al., "Removal of Chlorinated Organic Impurities from Hydrogen Chloride," CA, Jan. 1, 1900, XP002352444 (English CA Summary only).

Myszkowski J. et al., "Removal of Organic Compoiunds from Gaseous Hydrogen Chloride by an Absorption Method," CA, Jan. 1, 1900, XP002352445 (English CA summary only).

Milchert E. et al., "Recovering Hydrogen Chloride and Organic Chlor Compounds from the Reaction Mixture in the Chlorination of Ethylene," CA, Jan. 1, 1900, XP002352443 (English CA summary only).

Laine D.F., et al., "The Destruction of Organic Pollutants Under Mild Reaction Conditions ; A Review," Microchemical Journal, vol. 85, No. 2, 2006, pp. 183-193.

Rainwater Harvesting and Utilization, Internet Citation, XP003003726, 2000.

H. Galeman, Organic Synthesis, Section 1, pp. 234-235, 1946.

Chemical Encyclopedia 5, p. 457, 1979.

Exopy Resins, Sanghai Resin Plant, Shangai People's Press, 1971.

Martinetti Richard et al., "Environment Le Recyclage De l'eau," Industrie Textile, Ste. Sippe Sari, Metz, FR., No. 1300, Jul. 1, 1998, ISSN: 0019-9176.

W. Giger et al., "14C/12C-Ratios in Organic Matter and Hydrocarbons Extracted from Dated Lake Sediments," Nuclear Instruments and Methods in Physics Research B5 (1984), 394-397, XP-002631954.

Jurgen O. Metzger, "Fats and Oils as Renewable Feedstock for Chemistry," Eur. J. Lipid Sci. Technol. (2009), 111, 865-876, XP-002631953.

Bruce M. Bell, "Glycerin as a Renewable Feedstock for Epichlorohydrin Production. The GTE Process," Clean-Soil, Air, Water, vol. 36, No. 8 (2008) pp. 657-661. XP-002631952.

Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.

U.S. Appl. No. 13/131,516, filed May 26, 2011, Gilbeau et al.

* cited by examiner

METHOD FOR PREPARING CHLOROHYDRIN BY CONVERTING POLYHYDROXYLATED ALIPHATIC HYDROCARBONS

The present patent application is a 371 of PCT/EP06/62461, filed May 19, 2006. The present patent application also claims the benefit of patent application FR 05.05120 and of patent application EP 05104321.4, both filed on 20 May 2005, and of provisional U.S. patent applications 60/734,659, 60/734,627, 60/734,657, 60/734,658, 60/734,635, 60/734,634, 60/734,637 and 60/734,636, all filed on 8 Nov. 2005, the content of all of which is incorporated here by reference.

The present invention relates to a process for preparing a chlorohydrin by converting polyhydroxylated aliphatic hydrocarbons, more specifically by chlorinating polyhydroxylated aliphatic hydrocarbons.

Chlorohydrins are reaction intermediates in the preparation of epoxides. Dichloropropanol, for example, is a reaction intermediate in the preparation of epichlorohydrin and of epoxy resins (Kirk-Othmer Encyclopedia of Chemical Technology, Fourth Edition, 1992, Vol. 2, page 156, John Wiley & Sons, Inc.).

According to known processes it is possible to obtain dichloropropanol in particular by hypochlorinating allyl chloride, by chlorinating allyl alcohol and by hydrochlorinating glycerol. This latter process has the advantage that the dichloropropanol can be obtained starting from fossil raw materials or from renewable raw materials, and it is known that natural petrochemical resources, from which the fossil materials are obtained, such as petroleum, natural gas or coal, for example, are limited in their terrestrial availability.

Application WO 2005/054167 of SOLVAY SA describes a process for preparing dichloropropanol by reacting glycerol with hydrogen chloride in the presence of an acid, such as adipic acid, as catalyst. In this process the dichloropropanol is separated from the other products of the reaction, and these products are recycled to the glycerol chlorination reactor. It is possible to withdraw a fraction of these other reaction products via a purge and to subject said fraction to various treatments prior to possible discharge. Discharge does not constitute an acceptable solution from an environmental standpoint. Moreover, the extra cost associated with the pre-discharge treatment may be prohibitive for the economics of the process.

The objective of the invention is to provide a process for preparing a chlorohydrin that does not exhibit these drawbacks.

The invention accordingly provides a process for preparing a chlorohydrin in which a polyhydroxylated aliphatic hydrocarbon, an ester of a polyhydroxylated aliphatic hydrocarbon or a mixture thereof whose total metal content, expressed in elemental form, is greater than or equal to 0.1 µg/kg and less than or equal to 1000 mg/kg is reacted with a chlorinating agent.

It has been found that, by using a polyhydroxylated aliphatic hydrocarbon, an ester of a polyhydroxylated aliphatic hydrocarbon or a mixture thereof having a metal content, expressed in elemental form, of greater than or equal to 0.1 µg/kg and less than or equal to 1000 mg/kg, it is possible to subject the purges from the process to oxidation at a temperature greater than or equal to 800° C., and to obtain the following advantages:
1) recovery of the chlorinating agent;
2) recovery of the useful energy content of the reaction by-products;
3) reduction in the amount and toxicity of the by-products for discharge.

Without wishing to be tied by any particular theoretical explanation, it is thought that oxidation at a temperature greater than or equal to 800° C. may be conducted under satisfactory conditions because the reactions between the refractory materials making up the oxidation plant and the metals present in the purges are reduced by virtue of the low metal content of the by-products formed in the process. There is also avoidance of blockages within the oxidation plant.

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon bearing the hydroxyl functional group (OH) cannot possess more than one OH group and must have sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including the higher, vicinal or contiguous orders of these repeating units. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms, including, for example, heteroatoms of halogen, sulphur, phosphorus, nitrogen, oxygen, silicon and boron type, and mixtures thereof.

Polyhydroxylated aliphatic hydrocarbons which can be used in the present invention comprise, for example, 1,2-ethanediol (ethylene glycol), 1,2-propanediol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclohexanedimethanol, 1,2,3-propanetriol (also known as "glycerol" or "glycerin"), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol, and mixtures of at least two thereof. 1,2,3-Propanetriol or glycerol is the most preferred.

The esters of the polyhydroxylated aliphatic hydrocarbon may be present in the polyhydroxylated aliphatic hydrocarbon and/or may be produced in the process for preparing the chlorohydrin and/or may be prepared prior to the process for preparing the chlorohydrin. Examples of esters of the polyhydroxylated aliphatic hydrocarbon comprise ethylene glycol monoacetate, propanediol monoacetates, glycerol monoacetates, glycerol monostearates, glycerol diacetates and mixtures thereof.

The term "chlorohydrin" is used here in order to describe a compound containing at least one hydroxyl group and at least one chlorine atom attached to different saturated carbon atoms. A chlorohydrin which contains at least two hydroxyl groups is also a polyhydroxylated aliphatic hydrocarbon.

Accordingly the starting material and the product of the reaction may each be chlorohydrins. In that case the "product" chlorohydrin is more chlorinated than the starting chlorohydrin, in other words has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The polyhydroxylated aliphatic hydrocarbon, the ester of polyhydroxylated aliphatic hydrocarbon, or the mixture thereof in the process according to the invention may be obtained starting from fossil raw materials or starting from renewable raw materials, preferably starting from renewable raw materials.

By fossil raw materials are meant materials obtained from the processing of petrochemical natural resources, such as petroleum, natural gas and coal, for example. Among these materials preference is given to organic compounds containing 2 and 3 carbon atoms. When the polyhydroxylated aliphatic hydrocarbon is glycerol, allyl chloride, allyl alcohol and "synthetic" glycerol are particularly preferred. By "synthetic" glycerol is meant a glycerol generally obtained from petrochemical resources. When the polyhydroxylated aliphatic hydrocarbon is ethylene glycol, ethylene and "synthetic" ethylene glycol are particularly preferred. By "synthetic" ethylene glycol is meant an ethylene glycol generally obtained from petrochemical resources. When the polyhydroxylated aliphatic hydrocarbon is propylene glycol, propylene and "synthetic" propylene glycol are particularly preferred. By "synthetic" propylene glycol is meant a propylene glycol generally obtained from petrochemical resources.

By renewable raw materials are meant materials obtained from the processing of renewable natural resources. Among these materials preference is given to "natural" ethylene glycol, "natural" propylene glycol and "natural" glycerol. "Natural" ethylene glycol, propylene glycol and glycerol are obtained for example by conversion of sugars by thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenation of xylose. The xylose may for example be obtained by hydrolysis of the hemicellulose present in maize fibres. By "natural glycerol" or "glycerol obtained from renewable raw materials" is meant, in particular, glycerol obtained during the production of biodiesel or else glycerol obtained during conversions of animal or vegetable oils or fats in general, such as saponification, transesterification or hydrolysis reactions.

Among the oils which can be used for preparing the natural glycerol, mention may be made of all common oils, such as palm oil, palm kernel oil, copra oil, babassu oil, former or new (low erucic acid) colza oil, sunflower oil, maize oil, castor oil and cotton oil, peanut oil, soya bean oil, linseed oil and crambe oil, and all oils obtained, for example, from sunflower plants or colza plants obtained by genetic modification or hybridization.

It is also possible to employ used frying oils, various animal oils, such as fish oils, tallow, lard and even squaring greases.

Among the oils used mention may also be made of oils which have been partly modified by means, for example, of polymerization or oligomerization, such as, for example, the "stand oils" of linseed oil and of sunflower oil, and blown vegetable oils.

A particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process can be a process for producing biodiesel.

In the process according to the invention it is preferred to use a polyhydroxylated aliphatic hydrocarbon, an ester of a polyhydroxylated aliphatic hydrocarbon or a mixture thereof which is obtained starting from renewable raw materials.

In the process for preparing a chlorohydrin according to the invention, the polyhydroxylated aliphatic hydrocarbon, the ester of polyhydroxylated aliphatic hydrocarbon or the mixture thereof may have an alkali metal and/or alkaline earth metal content of less than or equal to 1 g/kg, as described in the application entitled "Process for preparing a chlorohydrin by chlorinating a polyhydroxylated aliphatic hydrocarbon", filed in the name of SOLVAY SA on the same day as the present application, and whose content is incorporated here by reference. The alkali metals may be selected from lithium, sodium, potassium, rubidium and caesium and the alkaline earth metals may be selected from magnesium, calcium, strontium and barium.

In the process for preparing a chlorohydrin according to the invention, the polyhydroxylated aliphatic hydrocarbon, the ester of polyhydroxylated aliphatic hydrocarbon or the mixture thereof may contain metals other than the alkali metals and alkaline earth metals. Among such metals consideration may be given to iron, nickel, chromium, copper, lead, arsenic, cobalt, titanium, vanadium, tin, tellurium, cadmium, antimony, mercury, selenium, zinc, aluminium, and bismuth. The polyhydroxylated aliphatic hydrocarbon, the ester of polyhydroxylated aliphatic hydrocarbon or the mixture thereof may also contain elements other than the metals, such as, for example, sulphur and nitrogen.

In the process for preparing a chlorohydrin according to the invention, the polyhydroxylated aliphatic hydrocarbon, the ester of polyhydroxylated aliphatic hydrocarbon or the mixture thereof has a metal content of preferably less than or equal to 500 mg/kg, with more particular preference less than or equal to 150 mg/kg, with even more particular preference less than or equal to 50 mg/kg and very particular preference less than 15 mg/kg.

In the process for preparing a chlorohydrin according to the invention, the iron content of the polyhydroxylated aliphatic hydrocarbon, the ester of polyhydroxylated aliphatic hydrocarbon or the mixture thereof is less than or equal to 100 mg/kg, preferably less than or equal to 10 mg/kg and with particular preference less than or equal to 1 mg/kg. Said content is generally greater than or equal to 0.1 µg/kg.

In the process for preparing a chlorohydrin according to the invention, the nickel content of the polyhydroxylated aliphatic hydrocarbon, the ester of polyhydroxylated aliphatic hydrocarbon or the mixture thereof is less than or equal to 10 mg/kg, preferably less than or equal to 1 mg/kg and with particular preference less than or equal to 0.1 mg/kg. Said content is generally greater than or equal to 0.1 µg/kg.

In the process for preparing a chlorohydrin according to the invention, the chromium content of the polyhydroxylated aliphatic hydrocarbon, the ester of polyhydroxylated aliphatic hydrocarbon or the mixture thereof is less than or equal to 10 mg/kg, preferably less than or equal to 1 mg/kg and with particular preference less than or equal to 0.1 mg/kg. Said content is generally greater than or equal to 0.1 µg/kg.

In the process for preparing a chlorohydrin according to the invention, the copper content of the polyhydroxylated aliphatic hydrocarbon, the ester of polyhydroxylated aliphatic hydrocarbon or the mixture thereof is less than or equal to 10 mg/kg, preferably less than or equal to 1 mg/kg and with particular preference less than or equal to 0.25 mg/kg. Said content is generally greater than or equal to 0.1 µg/kg.

In the process for preparing a chlorohydrin according to the invention, the cumulative lead, arsenic and cobalt content of the polyhydroxylated aliphatic hydrocarbon, the ester of polyhydroxylated aliphatic hydrocarbon or the mixture thereof is less than or equal to 5 mg/kg, preferably less than or equal to 3 mg/kg and with particular preference less than or equal to 0.1 mg/kg. Said content is generally greater than or equal to 0.1 µg/kg.

In the process for preparing a chlorohydrin according to the invention, the titanium content of the polyhydroxylated aliphatic hydrocarbon, the ester of polyhydroxylated aliphatic hydrocarbon or the mixture thereof is less than or equal to 10 mg/kg, preferably less than or equal to 5 mg/kg and with particular preference less than or equal to 1 mg/kg. Said content is generally greater than or equal to 0.1 µg/kg.

In the process for preparing a chlorohydrin according to the invention, the cumulative titanium, vanadium, tin and tellurium content of the polyhydroxylated aliphatic hydrocarbon, the ester of polyhydroxylated aliphatic hydrocarbon or the mixture thereof is less than or equal to 10 mg/kg, preferably less than or equal to 5 mg/kg and with particular preference less than or equal to 0.1 mg/kg. Said content is generally greater than or equal to 0.1 µg/kg.

In the process for preparing a chlorohydrin according to the invention, the cumulative cadmium and antimony content of the polyhydroxylated aliphatic hydrocarbon, the ester of polyhydroxylated aliphatic hydrocarbon or the mixture thereof is less than or equal to 5 mg/kg, preferably less than or equal to 1 mg/kg and with particular preference less than or equal to 0.1 mg/kg. Said content is generally greater than or equal to 0.1 µg/kg.

In the process for preparing a chlorohydrin according to the invention, the mercury content of the polyhydroxylated aliphatic hydrocarbon, the ester of polyhydroxylated aliphatic hydrocarbon or the mixture thereof is less than or equal to 1 mg/kg, preferably less than or equal to 0.5 mg/kg and with particular preference less than or equal to 0.04 mg/kg. Said content is generally greater than or equal to 0.1 µg/kg.

In the process for preparing a chlorohydrin according to the invention, the zinc content of the polyhydroxylated aliphatic hydrocarbon, the ester of polyhydroxylated aliphatic hydrocarbon or the mixture thereof is less than or equal to 10 mg/kg, preferably less than or equal to 2 mg/kg and with particular preference less than or equal to 1 mg/kg. Said content is generally greater than or equal to 0.1 µg/kg.

In the process for preparing a chlorohydrin according to the invention, the cumulative selenium and zinc content of the polyhydroxylated aliphatic hydrocarbon, the ester of polyhydroxylated aliphatic hydrocarbon or the mixture thereof is less than or equal to 12 mg/kg, preferably less than or equal to 1 mg/kg and with particular preference less than or equal to 0.2 mg/kg. Said content is generally greater than or equal to 0.1 µg/kg.

In the process for preparing a chlorohydrin according to the invention, the cumulative sodium and calcium content of the polyhydroxylated aliphatic hydrocarbon, the ester of polyhydroxylated aliphatic hydrocarbon or the mixture thereof is less than or equal to 50 mg/kg, preferably less than or equal to 30 mg/kg and with particular preference less than or equal to 2.5 mg/kg. Said content is generally greater than or equal to 0.1 µg/kg.

In the process for preparing a chlorohydrin according to the invention, the aluminium content of the polyhydroxylated aliphatic hydrocarbon, the ester of polyhydroxylated aliphatic hydrocarbon or the mixture thereof is less than or equal to 10 mg/kg, preferably less than or equal to 5 mg/kg and with particular preference less than or equal to 1 mg/kg. Said content is generally greater than or equal to 0.1 µg/kg.

In the process for preparing a chlorohydrin according to the invention, the bismuth content of the polyhydroxylated aliphatic hydrocarbon, the ester of polyhydroxylated aliphatic hydrocarbon or the mixture thereof is less than or equal to 5 mg/kg, preferably less than or equal to 1 mg/kg and with particular preference less than or equal to 0.2 mg/kg. Said content is generally greater than or equal to 0.1 µg/kg.

In one particular embodiment of the process according to the invention, the polyhydroxylated aliphatic hydrocarbon, the ester of polyhydroxylated aliphatic hydrocarbon or the mixture thereof contains an amount of heavy compounds other than the polyhydroxylated aliphatic hydrocarbon and whose boiling temperature under a pressure of 1 bar absolute is at least 15° C. greater than the boiling temperature of the chlorohydrin of less than or equal to 50 g/kg.

In this particular embodiment the heavy compounds may be selected from fatty acids, their salts, their esters and mixtures thereof.

The fatty acids contain preferably at least 12 carbon atoms. Fatty acids and mixtures of fatty acids derived from vegetable oils and animal fats are preferred. Fatty acids and fatty acid mixtures derived from colza oil, sunflower oil, soybean oil and palm oil are particularly preferred. Oleic, linoleic, linolenic, palmitic and stearic acids and mixtures thereof are very particularly preferred. Oleic, linoleic and linolenic acids and mixtures thereof are especially suitable.

The salts of fatty acids are often alkali metal salts, alkaline earth metal salts and ammonium salts or mixtures thereof, and more particularly sodium, potassium and calcium salts.

The fatty acid esters may be selected from mono-, di- and triglycerides and the methyl esters of fatty acid, and mixtures thereof.

Without wishing to be tied by any particular theoretical explanation, it is thought that the heavy compounds present in the polyhydroxylated aliphatic hydrocarbon, the ester of polyhydroxylated aliphatic hydrocarbon or the mixture thereof accumulate in the recycled streams and make it necessary to increase the frequency of purge operations.

In the process for preparing a chlorohydrin according to the invention, the heavy compounds content of the polyhydroxylated aliphatic hydrocarbon, the ester of polyhydroxylated aliphatic hydrocarbon or the mixture thereof is preferably less than or equal to 30 g/kg, with more particular preference less than or equal to 10 g/kg, with still more particular preference less than or equal to 1 g/kg and with very particular preference less than or equal to 0.5 g/kg.

It is found that, by using a polyhydroxylated aliphatic hydrocarbon containing not more than 4 g/kg of heavy compounds as defined above, it is possible to reduce the volume of the purges.

In the process for preparing a chlorohydrin according to the invention, the polyhydroxylated aliphatic hydrocarbon, the ester of polyhydroxylated aliphatic hydrocarbon or the mixture thereof may be as specifically disclosed in application WO 2005/054167 of SOLVAY SA from page 2 line 8 to page 4 line 2.

In the process for preparing a chlorohydrin according to the invention, the polyhydroxylated aliphatic hydrocarbon, the ester of polyhydroxylated aliphatic hydrocarbon or the mixture thereof may or may not have undergone one or more purification treatments between its preparation and its use in the process according to the invention. Such treatments may be as described in application WO 2005/054167 of SOLVAY SA on page 3 lines 4 to 14 and lines 30 to 33.

Particular mention is made of purification treatments such as distillation, evaporation, extraction, adsorption or concentration operations followed by separating operations such as decantation, filtration or centrifugation. Mention is also made of purification operations by treatment with resins, preferably ion exchange resins.

Preference is given to using a polyhydroxylated aliphatic hydrocarbon, an ester of a polyhydroxylated aliphatic hydrocarbon or a mixture thereof which has not undergone such treatments.

When the polyhydroxylated aliphatic hydrocarbon is glycerol, it is preferred to use a glycerol obtained by a process of transesterification starting from renewable raw materials in the presence of a heterogeneous catalyst.

A glycerol of this kind may be obtained, for example, in the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and is employed in the form of a fixed bed. This latter process may be a biodiesel production process.

More particular preference is given to using a glycerol obtained by a process of transesterification starting from renewable raw materials in the presence of a heterogeneous catalyst selected from mixed oxides of aluminium and zinc, mixed oxides of zinc and titanium, mixed oxides of zinc, titanium and aluminium and mixed oxides of bismuth and aluminium in supported and unsupported form and the heterogeneous catalyst is employed in the form of a fixed bed.

This glycerol preparation process presents a number of advantages over processes based on saponification, transesterification or hydrolysis reactions which do not employ a heterogeneous catalyst:

A first advantage is that the contamination of the glycerol by metals is reduced. These metals may be alkali metals and/or alkaline earth metals originating, for example, from the basic reagents used in the saponification reactions (alkaline bases), in neutralizing operations using alkaline bases, or metals originating from homogeneous acidic catalysts used in transesterification or acidic hydrolysis reactions, or else metals originating from the corrosion of the glycerol preparation apparatus. The use of heterogeneous catalysts as described above makes it possible to reduce significantly the contamination of the glycerol by alkali metal and alkaline earth metal elements, and also by other metallic elements.

A second advantage is that the contamination of the glycerol by Matter (Organic) Non-Glycerol (MONG) is reduced. This matter (organic) non-glycerol contributes to a not insignificant extent to the heavy compounds as defined earlier on above, and include, for example, carboxylic acids, fatty acid esters such as the mono-, di- and triglycerides and the esters of fatty acids with the alcohols used in the transesterification. The MONG content of the glycerol in accordance with standard ISO 2464 (1973) is obtained by the following formula:

MONG (%)=100−[GLC]−[H$_2$O]−[dry residue]

where

[GLC] is the glycerol content of the glycerol (in %) as in the standardized method of ISO 2879 (1975)

[H$_2$O] is the water content (in %) of the glycerol, as assay by the Karl-Fischer method, described in the standardized method of ISO 2098 (1972)

[dry residue] is the dry residue content (in %) of the glycerol, obtained after calcination in accordance with the standardized method of ISO 2098 (1972).

The amount of matter (organic) non-glycerol in the glycerol is generally less than or equal to 5%, preferably less than or equal to 1% and with more particular preference less than or equal to 0.5%.

In the process for preparing dichloropropanol according to the invention, the amount of caustic soda consumed in determining the amount of fatty acids and fatty acid esters in accordance with standard USP24/NF19 is generally less than or equal to 30 milliequivalents/kg, preferably less than or equal to 3 milliequivalents/kg and with particular preference less than or equal to 2 milliequivalents/kg. This amount is generally greater than or equal to 0.2 milliequivalent/kg.

A third advantage is that the water content of the glycerol is reduced.

In the process for preparing dichloropropanol according to the invention, the water content of the glycerol is generally less than or equal to 100 g/kg, preferably less than or equal to 50 g/kg, with more particular preference less than or equal to 20 g/kg and with very particular preference less than or equal to 10 g/kg. Said content is generally greater than or equal to 500 mg/kg.

In the process for preparing a chlorohydrin according to the invention, the chlorinating agent may be as described in application WO 2005/054167 of SOLVAY SA, from page 4 line 25 to page 6 line 2.

In the process for preparing a chlorohydrin according to the invention, the chlorinating agent may be hydrogen chloride as described in application WO 2005/054167 of SOLVAY SA, from page 4 line 30 to page 6 line 2.

Particular mention is made of a chlorinating agent which may be aqueous hydrochloric acid or hydrogen chloride which is preferably anhydrous.

The hydrogen chloride may originate from a process for pyrolysing organic chlorine compounds, such as, for example, from a vinyl chloride production, from a process for producing 4,4-methylenediphenyl diisocyanate (MDI) or toluene diisocyanate (TDI), from metal pickling processes or from the reaction of an inorganic acid such as sulphuric or phosphoric acid with a metal chloride such as sodium chloride, potassium chloride or calcium chloride.

In one advantageous embodiment of the process for preparing a chlorohydrin according to the invention, the chlorinating agent is gaseous hydrogen chloride or an aqueous solution of hydrogen chloride, or a combination of the two.

In the process for preparing a chlorohydrin according to the invention, the hydrogen chloride may be an aqueous solution of hydrogen chloride or may be preferably anhydrous hydrogen chloride, obtained from a plant for producing allyl chloride and/or for producing chloromethanes and/or a chlorinolysis plant and/or a plant for high-temperature oxidation of chlorine compounds, as described in the application entitled "Process for preparing a chlorohydrin by reacting a polyhydroxylated aliphatic hydrocarbon with a chlorinating agent", filed in the name of SOLVAY SA on the same day as the present application, and the content of which is incorporated here by reference.

Particular mention is made of a process for preparing a chlorohydrin from a polyhydroxylated aliphatic hydrocarbon, from an ester of a polyhydroxylated aliphatic hydrocarbon or from a mixture thereof, and from a chlorinating agent, the chlorinating agent comprising at least one of the following compounds: nitrogen, oxygen, hydrogen, chlorine, an organic hydrocarbon compound, an organic halogen compound, an organic oxygen compound and a metal.

Particular mention is made of an organic hydrocarbon compound which is selected from saturated or unsaturated aliphatic and aromatic hydrocarbons and mixtures thereof.

Particular mention is made of an unsaturated aliphatic hydrocarbon which is selected from acetylene, ethylene, propylene, butene, propadiene, methylacetylene and mixtures thereof, of a saturated aliphatic hydrocarbon which is selected from methane, ethane, propane, butane and mixtures thereof and of an aromatic hydrocarbon which is benzene.

Particular mention is made of an organic halogen compound which is an organic chlorine compound selected from chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

Particular mention is made of an organic halogen compound which is an organic fluorine compound selected from fluoromethanes, fluoroethanes, vinyl fluoride, vinylidene fluoride and mixtures thereof.

Particular mention is made of an organic oxygen compound which is selected from alcohols, chloroalcohols, chloroethers and mixtures thereof.

Particular mention is made of a metal selected from alkali metals, alkaline earth metals, iron, nickel, copper, lead, arsenic, cobalt, titanium, cadmium, antimony, mercury, zinc, selenium, aluminium, bismuth and mixtures thereof.

Mention is made more particularly of a process wherein the chlorinating agent is obtained at least partly from a process for preparing allyl chloride and/or a process for preparing chloromethanes and/or a process of chlorinolysis and/or a process for oxidizing chlorine compounds at a temperature greater than or equal to 800° C.

In one particularly advantageous embodiment of the process for preparing a chlorohydrin according to the invention, the hydrogen chloride is an aqueous solution of hydrogen chloride and does not contain gaseous hydrogen chloride.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in a reactor as described in application WO 2005/054167 of SOLVAY SA on page 6 lines 3 to 23.

Mention is made particularly of a plant made of or covered with materials which are resistant, under the reaction conditions, to the chlorinating agents, particularly to hydrogen chloride. Mention is made more particularly of a plant made of enamelled steel or of tantalum.

In the process for preparing a chlorohydrin according to the invention, the reaction of the polyhydroxylated aliphatic hydrocarbon, the ester of the polyhydroxylated aliphatic hydrocarbon or the mixture thereof with the chlorinating agent may be carried out in apparatus which is made of or covered with materials that are resistant to chlorinating agents, as described in the patent application entitled "Process for preparing a chlorohydrin in corrosion-resistant apparatus", filed in the name of SOLVAY SA on the same day as the present application, and the content of which is incorporated here by reference.

Particular mention is made of a process for preparing a chlorohydrin that includes a step in which a polyhydroxylated aliphatic hydrocarbon, an ester of a polyhydroxylated aliphatic hydrocarbon or a mixture thereof is subjected to reaction with a chlorinating agent containing hydrogen chloride and to at least one other step carried out in an apparatus made of or covered with materials resistant to the chlorinating agent, under the conditions in which that step is realized. Mention is made more particularly of metallic materials such as enamelled steel, gold and tantalum and of non-metallic materials such as high-density polyethylene, polypropylene, poly(vinylidene fluoride), polytetrafluoroethylene, perfluoroalkoxyalkanes and poly(perfluoropropyl vinyl ether), polysulphones and polysulphides, and unimpregnated and impregnated graphite.

In the process for preparing a chlorohydrin according to the invention, the reaction of the polyhydroxylated aliphatic hydrocarbon with the chlorinating agent may be carried out in a reaction medium as described in the application entitled "Continuous process for preparing chlorohydrins" filed in the name of SOLVAY SA on the same day as the present application, and the content of which is incorporated here by reference.

Particular mention is made of a continuous process for preparing a chlorohydrin wherein a polyhydroxylated aliphatic hydrocarbon, an ester of a polyhydroxylated aliphatic hydrocarbon or a mixture thereof is reacted with a chlorinating agent and an organic acid in a liquid reaction medium whose steady-state composition includes the polyhydroxylated aliphatic hydrocarbon and esters of the polyhydroxylated aliphatic hydrocarbon whose sum content, expressed as moles of polyhydroxylated aliphatic hydrocarbon, is greater than 1.1 mol % and less than or equal to 30 mol %, the percentage being based on the organic part of the liquid reaction medium.

In the process for preparing a chlorohydrin according to the invention, the reaction of the polyhydroxylated aliphatic hydrocarbon, the ester of polyhydroxylated aliphatic hydrocarbon or the mixture thereof and the chlorinating agent may be carried out in the presence of a catalyst as described in application WO 2005/054167 of SOLVAY SA from page 6 line 28 to page 8 line 5.

Mention is made particularly of a catalyst based on a carboxylic acid or on a carboxylic acid derivative having an atmospheric boiling point of greater than or equal to 200° C., especially adipic acid and derivatives of adipic acid.

In the process for preparing a chlorohydrin according to the invention, the reaction of the polyhydroxylated aliphatic hydrocarbon, the ester of polyhydroxylated aliphatic hydrocarbon or the mixture thereof and the chlorinating agent may be carried out at a catalyst concentration, temperature and pressure and for residence times as described in the application WO 2005/054167 of SOLVAY SA from page 8 line 6 to page 10 line 10.

Mention is made particularly of a temperature of at least 20° C. and not more than 160° C., of a pressure of at least 0.3 bar and not more than 100 bar and of a residence time of at least 1 h and not more than 50 h.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a solvent as described in application WO 2005/054167 of SOLVAY SA at page 11 lines 12 to 36.

Mention is made particularly of organic solvents such as a chlorinated organic solvent, an alcohol, a ketone, an ester or an ether, a non-aqueous solvent which is miscible with the polyhydroxylated aliphatic hydrocarbon, such as chloroethanol, chloropropanol, chloropropanediol, dichloropropanol, dioxane, phenol, cresol and mixtures of chloropropanediol and dichloropropanol, or heavy products of the reaction such as at least partially chlorinated and/or esterified oligomers of the polyhydroxylated aliphatic hydrocarbon.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a liquid phase comprising heavy compounds other than the polyhydroxylated aliphatic hydrocarbon, as described in the application entitled "Process for preparing a chlorohydrin in a liquid phase", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of polyhydroxylated aliphatic hydrocarbon or a mixture thereof is subjected to reaction with a chlorinating agent in the presence of a liquid phase comprising heavy compounds other than the polyhydroxylated aliphatic hydrocarbon and having a boiling temperature under a pressure of 1 bar absolute of at least 15° C. more than the boiling temperature of the chlorohydrin under a pressure of 1 bar absolute.

In the process for preparing a chlorohydrin according to the invention the reaction of the polyhydroxylated aliphatic hydrocarbon, the ester of polyhydroxylated aliphatic hydrocarbon or the mixture thereof with the chlorinating agent is preferably carried out in a liquid reaction medium. The liquid reaction medium may be a single-phase or multi-phase medium.

The liquid reaction medium is composed of all of the dissolved or dispersed solid compounds, dissolved or dispersed liquid compounds and dissolved or dispersed gaseous compounds at the temperature of the reaction.

The reaction medium comprises the reactants, the catalyst, the solvent, the impurities present in the reactants, in the solvent and in the catalyst, the reaction intermediates, the products and the by-products of the reaction.

By reactants are meant the polyhydroxylated aliphatic hydrocarbon, the ester of polyhydroxylated aliphatic hydrocarbon and the chlorinating agent.

Among the impurities present in the polyhydroxylated aliphatic hydrocarbon mention may be made of carboxylic acids, salts of carboxylic acids, esters of fatty acid with the polyhydroxylated aliphatic hydrocarbon, esters of fatty acids with the alcohols used in the transesterification, and inorganic salts such as alkali metal or alkaline earth metal sulphates and chlorides.

When the polyhydroxylated aliphatic hydrocarbon is glycerol, the impurities in the glycerol that may be mentioned include carboxylic acids, salts of carboxylic acids, fatty acid esters such as mono-, di- and triglycerides, esters of fatty acids with the alcohols used in the transesterification and inorganic salts such as alkali metal or alkaline earth metal sulphates and chlorides.

Among the reaction intermediates mention may be made of monochlorohydrins of the polyhydroxylated aliphatic hydrocarbon and their esters and/or polyesters, the esters and/or polyesters of the polyhydroxylated aliphatic hydrocarbon and the esters of polychlorohydrins.

When the chlorohydrin is dichloropropanol, the reaction intermediates that may be mentioned include glycerol monochlorohydrin and its esters and/or polyesters, the esters and/or polyesters of glycerol and the esters of dichloropropanol.

By products of the reaction are meant the chlorohydrin and water. The water may be the water formed in the chlorination reaction and/or water introduced into the process, for example via the polyhydroxylated aliphatic hydrocarbon and/or the chlorinating agent, as described in the application WO 2005/054167 of SOLVAY SA at page 2 lines 22 to 28 to page 3 lines 20 to 25, at page 5 lines 7 to 31 and at page 12 lines 14 to 19.

Among the by-products mention may be made for example of the partially chlorinated and/or esterified oligomers of the polyhydroxylated aliphatic hydrocarbon.

When the polyhydroxylated aliphatic hydrocarbon is glycerol, the by-products that may be mentioned include, for example, the partially chlorinated and/or esterified oligomers of glycerol.

The reaction intermediates and the by-products may be formed in the different steps of the process, such as, for example, during the step of preparing the chlorohydrin and during the steps of separating off the chlorohydrin.

The ester of polyhydroxylated aliphatic hydrocarbon may therefore be, at each instance, a reactant, an impurity of the polyhydroxylated aliphatic hydrocarbon or a reaction intermediate.

The liquid reaction medium may therefore contain the polyhydroxylated aliphatic hydrocarbon, the chlorinating agent in solution or dispersion in the form of bubbles, the catalyst, the solvent, the impurities present in the reactants, in the solvent and in the catalyst, such as dissolved or solid salts, for example, the reaction intermediates, the products and the by-products of the reaction.

The process according to the invention may be carried out in batch mode or in continuous mode. The continuous mode is particularly preferred.

In the preparation process according to the invention, the reaction of the polyhydroxylated aliphatic hydrocarbon with the chlorinating agent may take place in the presence of an organic acid. The organic acid may be a product originating from the process for preparing the polyhydroxylated aliphatic hydrocarbon, or may be a product not originating from that process. In this latter case the acid may be an organic acid used to catalyse the reaction between the polyhydroxylated aliphatic hydrocarbon and the chlorinating agent. The organic acid may also be a mixture of organic acid originating from the process for preparing the polyhydroxylated aliphatic hydrocarbon with an organic acid not originating from the process for preparing the polyhydroxylated aliphatic hydrocarbon.

In the process according to the invention, the separation of the chlorohydrin and of the other compounds from the reaction mixture may be carried out in accordance with the methods as described in the application WO 2005/054167 of SOLVAY SA from page 12 line 1 to page 16 line 35 and page 18 lines 6 to 13. These other compounds are those mentioned above and include unconsumed reactants, the impurities present in the reactants, the catalyst and the solvent, the solvent, the catalyst, the reaction intermediates, the water and the by-products of the reaction.

Particular mention is made of separation by azeotropic distillation of a water/chlorohydrin/chlorinating agent mixture under conditions which minimize the losses of chlorinating agent, followed by isolation of the chlorohydrin by decantation.

In the process for preparing a chlorohydrin according to the invention, the isolation of the chlorohydrin and of the other compounds from the reaction mixture from chlorination of the polyhydroxylated aliphatic hydrocarbon may be carried out in accordance with methods of the kind described in patent application EP 05104321.4, filed in the name of SOLVAY SA on 20 May 2005 and the content of which is incorporated here by reference. A separation method including at least one separating operation intended to remove the salt from the liquid phase is particularly preferred.

Particular mention is made of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon that is used comprises at least one solid or dissolved metal salt, the process including a separation operation intended to remove part of the metal salt. Mention is made more particularly of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, the ester of polyhydroxylated aliphatic hydrocarbon or mixture thereof that is used comprises at least one chloride and/or a sodium and/or potassium sulphate and in which the separating operation intended to remove part of the metal salt is a filtering operation. Particular mention is also made of a process for preparing a chlorohydrin wherein (a) a polyhydroxylated aliphatic hydrocarbon, an ester of a polyhydroxylated aliphatic hydrocarbon or a mixture thereof is subjected to reaction with a chlorinating agent in a reaction mixture, (b) continuously or periodically, a fraction of the reaction mixture containing at least water and the chlorohydrin is removed, (c) at least a part of the fraction obtained in step (b) is introduced into a distillation step and (d) the reflux ratio of the distillation step is controlled by providing water to the said distillation step. Mention is made very particularly of a process for preparing a chlorohydrin wherein (a) a polyhydroxylated aliphatic hydrocarbon, an ester of a polyhydroxylated aliphatic hydrocarbon or a mixture thereof is subjected to reaction with hydrogen chloride in a reaction mixture, (b) continuously or periodically, a fraction of the reaction mixture containing at least water and chlorohydrin is removed, (c) at least part of the fraction obtained in step (b) is introduced into a distillation step in which the ratio between the hydrogen chloride concentration and the water concentration in the fraction introduced into the distillation step is smaller than the hydrogen chloride/water concentration ratio in the binary azeotropic hydrogen chloride/water composition at the distillation temperature and pressure.

In the process for preparing a chlorohydrin according to the invention, the separation of the chlorohydrin and of the other compounds from the reaction mixture from chlorination of the polyhydroxylated aliphatic hydrocarbon may be carried out in accordance with methods as described in the application entitled "Process for preparing a chlorohydrin", filed in the name of SOLVAY SA on the same day as the present application, and the content of which is incorporated here by reference.

Particular mention is made of a process for preparing a chlorohydrin which comprises the following steps: (a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of the chlorohydrin, (b) at least part of the mixture obtained in (a) is subjected to one or more treatments subsequent to step (a), and (c) the polyhydroxylated aliphatic hydrocarbon is added to at least one of the steps subsequent to step (a), in order to react at a temperature greater than or equal to 20° C. with the esters of the chlorohydrin, so as to form, at least partly, esters of the polyhydroxylated aliphatic hydrocarbon. Mention is made more particularly of a process in which the polyhydroxylated aliphatic hydrocarbon is glycerol and the chlorohydrin is dichloropropanol.

In the process for preparing a chlorohydrin according to the invention, the separation of the chlorohydrin and the other compounds from the reaction mixture from chlorination of the polyhydroxylated aliphatic hydrocarbon may be carried out in accordance with methods as described in the application entitled "Process for preparing a chlorohydrin starting from a polyhydroxylated aliphatic hydrocarbon", filed in the name of SOLVAY SA on the same day as the present application, and the content of which is incorporated here by reference.

Particular mention is made of a process for preparing chlorohydrin by reacting a polyhydroxylated aliphatic hydrocarbon, an ester of a polyhydroxylated aliphatic hydrocarbon or a mixture thereof with a chlorinating agent in a reactor which is supplied with one or more liquid streams containing less than 50% by weight of the polyhydroxylated aliphatic hydrocarbon, of the ester of polyhydroxylated aliphatic hydrocarbon or of the mixture thereof relative to the weight of the entirety of the liquid streams introduced into the reactor. More particular mention is made of a process comprising the following steps: (a) a polyhydroxylated aliphatic hydrocarbon, an ester of a polyhydroxylated aliphatic hydrocarbon or a mixture thereof is reacted with a chlorinating agent so as to give at least one mixture containing the chlorohydrin, water and the chlorinating agent, (b) at least a fraction of the mixture formed in step (a) is removed, and (c) the fraction removed in step (b) is subjected to an operation of distillation and/or stripping wherein the polyhydroxylated aliphatic hydrocarbon is added in order to isolate, from the fraction removed in step (b), a mixture containing water and the chlorohydrin and exhibiting a reduced chlorinating agent content as compared with the fraction removed in step (b).

In the process for preparing a chlorohydrin according to the invention, the separation of the chlorohydrin and of the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for converting polyhydroxylated aliphatic hydrocarbons into chlorohydrins", filed in the name of SOLVAY SA on the same day as the present application, and the content of which is incorporated here by reference. Particular mention is made of a process for preparing a chlorohydrin that comprises the following steps:

(a) A polyhydroxylated aliphatic hydrocarbon, an ester of a polyhydroxylated aliphatic hydrocarbon or a mixture thereof is reacted with a chlorinating agent so as to give a mixture containing the chlorohydrin, chlorohydrin esters and water.

(b) At least a fraction of the mixture obtained in step (a) is subjected to a distillation and/or stripping treatment so as to give a portion concentrated in water, in chlorohydrin and in chlorohydrin esters.

(c) At least a fraction of the portion obtained in step (b) is subjected to a separating operation in the presence of at least one additive so as to obtain a moiety concentrated in chlorohydrin and in chlorohydrin esters and containing less than 40% by weight of water.

The separating operation is more particularly a decantation.

In the process for preparing a chlorohydrin according to the invention, the isolation and the treatment of the other compounds of the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for preparing a chlorohydrin by chlorinating a polyhydroxylated aliphatic hydrocarbon", filed in the name of SOLVAY SA on the same day as the present application. A preferred treatment consists in subjecting a fraction of the by-products of the reaction to a high-temperature oxidation.

Particular mention is made of a process for preparing a chlorohydrin that comprises the following steps: (a) a polyhydroxylated aliphatic hydrocarbon, an ester of a polyhydroxylated aliphatic hydrocarbon or a mixture thereof whose alkali metal and/or alkaline earth metal content is less than or equal to 5 g/kg, a chlorinating agent and an organic acid are reacted so as to give a mixture containing at least the chlorohydrin and by-products, (b) at least a portion of the mixture obtained in step (a) is subjected to one or more treatments in steps subsequent to step (a), and (c) at least one of the steps subsequent to step (a) consists in an oxidation at a temperature greater than or equal to 800° C. More particular mention is made of a process wherein, in the subsequent step, a portion of the mixture obtained in step (a) is removed and this portion is subjected to oxidation at a temperature greater than or equal to 800° C. in the course of the removal. Particular mention is also made of a process wherein the treatment of step (b) is a separating operation selected from phase separation, filtration, centrifugation, extraction, washing, evaporation, stripping, distillation, and adsorption operations or the combinations of at least two of these operations.

In the process according to the invention, when the chlorohydrin is chloropropanol, it is generally obtained in the form of a mixture of compounds comprising the isomers of 1-chloropropan-2-ol and 2-chloropropan-1-ol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanol, such as residual reactants, reaction by-products, solvents and, in particular, water.

The mass ratio of the isomers, 1-chloropropan-2-ol and 2-chloropropan-1-ol, is commonly greater than or equal to 0.01, preferably greater than or equal to 0.4. This ratio is commonly less than or equal to 99 and preferably less than or equal to 25.

In the process according to the invention, when the chlorohydrin is chloroethanol, it is generally obtained in the form of a mixture of compounds comprising the 2-chloroethanol isomer. This mixture generally contains more than 1% by weight of the isomer, preferably more than 5% by weight and particularly more than 50%. The mixture commonly contains less than 99.9% by weight of the isomer, preferably less than 95% by weight and more particularly less than 90% by weight. The other constituents of the mixture may be compounds originating from the processes for preparing the chloroethanol, such as residual reactants, reaction by-products, solvents and, in particular, water. In the process according to the invention, when the chlorohydrin is dichloropropanol, it is generally obtained in the form of a mixture of compounds comprising the isomers of 1,3-dichloropropan-2-ol and 2,3-dichloropropan-1-ol. This mixture generally contains more than 1% by weight of the two isomers, preferably more than 5% by weight and in particular more than 50%. The mixture commonly contains less than 99.9% by weight of the two isomers, preferably less than 95% by weight and more particularly less than 90% by weight. The other constituents of the mixture may be compounds originating from the processes for preparing the dichloropropanol, such as residual reactants, reaction by-products, solvents and, in particular, water.

The mass ratio between the 1,3-dichloropropan-2-ol and 2,3-dichloropropan-1-ol isomers is commonly greater than or equal to 0.01, often greater than or equal to 0.4, frequently greater than or equal to 1.5, preferably greater than or equal to 3.0, more preferably greater than or equal to 7.0 and with very particular preference greater than or equal to 20.0. This ratio is commonly less than or equal to 99 and preferably less than or equal to 25.

In the process according to the invention, when the chlorohydrin is dichloropropanol and is obtained in a process starting from allyl chloride, the mixture of isomers has a 1,3-dichloropropan-2-ol:2,3-dichloropropan-1-ol mass ratio which is often from 0.3 to 0.6, typically approximately 0.5. When the dichloropropanol is obtained in a process starting from synthetic and/or natural glycerol, the 1,3-dichloropropan-2-ol:2,3-dichloropropan-1-ol mass ratio is commonly greater than or equal to 1.5, preferably greater than or equal to 3.0 and very particularly greater than or equal to 9.0. When the dichloropropanol is obtained starting from allyl alcohol, the 1,3-dichloropropan-2-ol:2,3-dichloropropan-1-ol mass ratio is often of the order of 0.1.

In the process according to the invention, when the chlorohydrin is dichloropropanol, the mixture of isomers has a 1,3-dichloropropan-2-ol:2,3-dichloropropan-1-ol mass ratio which is generally greater than or equal to 0.5, often greater than or equal to 3 and frequently greater than or equal to 20.

In the process for preparing a chlorohydrin according to the invention, the chlorohydrin may include a heightened amount of halogenated ketones, in particular of chloroacetone, as described in the patent application FR 05.05120 of 2 May 2005, filed in the name of the applicant, and the content of which is incorporated here by reference. The halogenated ketone content may be reduced by subjecting the chlorohydrin obtained in the process according to the invention to an azeotropic distillation in the presence of water or by subjecting the chlorohydrin to a dehydrochlorination treatment as described in this application from page 4 line 1 to page 6 line 35.

Particular mention is made of a process for preparing an epoxide wherein halogenated ketones are formed as by-products and which comprises at least one treatment of removal of at least a portion of the halogenated ketones formed. Mention is made more particularly of a process for preparing an epoxide by dehydrochlorinating a chlorohydrin of which at least one fraction is prepared by chlorinating a polyhydroxylated aliphatic hydrocarbon, an ester of a polyhydroxylated aliphatic hydrocarbon or a mixture thereof, a treatment of dehydrochlorination and a treatment by azeotropic distillation of a water/halogenated ketone mixture, which are intended to remove at least a portion of the halogenated ketones formed, and a process for preparing epichlorohydrin wherein the halogenated ketone formed is chloroacetone.

In the process for preparing a chlorohydrin according to the invention, the chlorohydrin may be subjected to a dehydrochlorination reaction in order to produce an epoxide, as described in the patent applications WO 2005/054167 and FR 05.05120, both filed in the name of SOLVAY SA.

The term "epoxide" is used herein to describe a compound containing at least one oxygen bridged on a carbon-carbon bond. Generally speaking, the carbon atoms of the carbon-carbon bond are adjacent and the compound may contain atoms other than carbon atoms and oxygen atoms, such as hydrogen atoms and halogens. The preferred epoxides are ethylene oxide, propylene oxide, glycidol and epichlorohydrin, and mixtures of at least two thereof.

The dehydrochlorination of the chlorohydrin may be carried out as described in the application entitled "Process for preparing an epoxide starting from a polyhydroxylated aliphatic hydrocarbon and a chlorinating agent", filed in the name of SOLVAY SA on the same day as the present application, and the content of which is incorporated here by reference.

Particular mention is made of a process for preparing an epoxide wherein a reaction mixture resulting from the reaction between a polyhydroxylated aliphatic hydrocarbon, an ester of a polyhydroxylated aliphatic hydrocarbon or a mixture thereof with a chlorinating agent, the reaction mixture containing at least 10 g of chlorohydrin per kg of reaction mixture, is subjected to a subsequent chemical reaction without intermediate treatment.

Mention is also made of the preparation of an epoxide that comprises the following steps:

(a) A polyhydroxylated aliphatic hydrocarbon, an ester of a polyhydroxylated aliphatic hydrocarbon or a mixture thereof is reacted with a chlorinating agent and an organic acid so as to form the chlorohydrin and chlorohydrin esters in a reaction mixture containing the polyhydroxylated aliphatic hydrocarbon, the ester of polyhydroxylated aliphatic hydrocarbon, water, the chlorinating agent and the organic acid, the reaction mixture containing at least 10 g of chlorohydrin per kg of reaction mixture.

(b) At least a fraction of the reaction mixture obtained in step (a), this fraction having the same composition as the reaction mixture obtained in step (a), is subjected to one or more treatments in steps subsequent to step (a).

(c) A basic compound is added to at least one of the steps subsequent to step (a) in order to react at least partly with the chlorohydrin, the chlorohydrin esters, the chlorinating agent and the organic acid so as to form the epoxide and salts.

The process for preparing the chlorohydrin according to the invention, may be integrated within an overall plan for preparation of an epoxide, as described in the application entitled "Process for preparing an epoxide starting from a chlorohydrin", filed in the name of SOLVAY SA on the same day as the present application, and the content of which is incorporated here by reference.

Particular mention is made of a process for preparing an epoxide that comprises at least one step of purification of the epoxide formed, the epoxide being at least partly prepared by a process of dehydrochlorinating a chlorohydrin, the latter being at least partly prepared by a process of chlorinating a polyhydroxylated aliphatic hydrocarbon, an ester of a polyhydroxylated aliphatic hydrocarbon or a mixture thereof.

In the process for preparing a chlorohydrin according to the invention, the polyhydroxylated aliphatic hydrocarbon is preferably glycerol and the chlorohydrin is preferably dichloropropanol.

When the chlorohydrin is dichloropropanol, the process according to the invention may be followed by preparation of epichlorohydrin by dehydrochlorination of dichloropropanol, and the epichlorohydrin may be used in the production of epoxy resins.

The invention claimed is:

1. A process for preparing dichloropropanol wherein glycerol whose total metal content, expressed in elemental form, is greater than or equal to 0.1 µg/kg and less than or equal to 500 mg/kg is reacted with a chlorinating agent,
wherein said process is further characterized by at least one of the following features:
the iron content of the glycerol is less than or equal to 100 mg/kg
the nickel content of the glycerol is less than or equal to 10 mg/kg
the chromium content of the glycerol is less than or equal to 10 mg/kg
the copper content of the glycerol is less than or equal to 10 mg/kg
the cumulative lead, arsenic and cobalt content of the glycerol is less than or equal to 5 mg/kg
the titanium content of the glycerol is less than or equal to 10 mg/kg
the cumulative titanium, vanadium, tin and tellurium content of the glycerol is less than or equal to 10 mg/kg
the cumulative cadmium and antimony content of the glycerol is less than or equal to 5 mg/kg
the mercury content of the glycerol is less than or equal to 1 mg/kg
the zinc content of the glycerol is less than or equal to 10 mg/kg
the cumulative selenium and zinc content of the glycerol is less than or equal to 12 mg/kg
the cumulative sodium and calcium content of the glycerol is less than or equal to 50 mg/kg
the aluminium content of the glycerol is less than or equal to 10 mg/kg, and
the bismuth content of the glycerol is less than or equal to 5 mg/kg.

2. The process according to claim 1, wherein said process exhibits at least one of the following features:
the iron content of the glycerol is less than or equal to 100 mg/kg
the nickel content of the glycerol is less than or equal to 10 mg/kg
the chromium content of the glycerol is less than or equal to 10 mg/kg
the copper content of the glycerol is less than or equal to 10 mg/kg
the cumulative lead, arsenic and cobalt content of the glycerol is less than or equal to 5 mg/kg
the titanium content of the glycerol is less than or equal to 10 mg/kg, and
the cumulative titanium, vanadium, tin and tellurium content of the glycerol is less than or equal to 10 mg/kg.

3. The process according to claim 1, wherein present in the glycerol is less than or equal to 50 g/kg of one or more heavy compounds other than glycerol whose boiling temperature under a pressure of 1 bar absolute is at least 15° C. greater than the boiling temperature of dichloropropanol.

4. The process according to claim 3, wherein the heavy compounds are selected from fatty acids, their salts, their esters and mixtures of at least two thereof.

5. The process according to claim 4, wherein the fatty acids comprise at least 12 carbon atoms in their molecule.

6. The process according to claim 5, wherein the fatty acids are selected from linoleic acid, oleic acid, linolenic acid, palmitic acid, stearic acid and mixtures of at least two thereof.

7. The process according to claim 6, wherein the fatty acids are selected from linoleic acid, oleic acid, linolenic acid and mixtures of at least two thereof.

8. The process according to claim 4, wherein the esters are mono-, di- and/or triglycerides or methyl esters of fatty acids.

9. The process according to claim 1, wherein the water content of the glycerol is less than or equal to 100 g/kg.

10. The process according to claim 1, wherein the glycerol is obtained by a process of transesterification starting from renewable raw materials in the presence of a heterogeneous catalyst,
wherein the heterogeneous catalyst is selected from mixed oxides of aluminium and zinc, mixed oxides of zinc and titanium, mixed oxides of zinc, titanium and aluminium and mixed oxides of bismuth and aluminium in supported and unsupported form and is employed in the form of a fixed bed.

11. The process according to claim 1, further comprising preparation of epichlorohydrin by dehydrochlorination of dichloropropanol.

12. The process according to claim 11, wherein the epichlorohydrin is used in the production of epoxy resins.

13. The process according to claim 1, wherein the chlorinating agent comprises hydrogen chloride.

14. The process according to claim 13, wherein the hydrogen chloride is a combination of gaseous hydrogen chloride and an aqueous solution of hydrogen chloride, or an aqueous solution of hydrogen chloride.

15. The process according to claim 1, wherein the total metal content of the glycerol, expressed in elemental form, is greater than or equal to 0.1 µg/kg and less than or equal to 150 mg/kg.

16. The process according to claim 1, wherein the total metal content of the glycerol, expressed in elemental form, is greater than or equal to 0.1 µg/kg and less than or equal to 50 mg/kg.

17. The process according to claim 1, wherein the total metal content of the glycerol, expressed in elemental form, is greater than or equal to 0.1 µg/kg and less than or equal to 15 mg/kg.

18. A process for preparing dichloropropanol wherein glycerol whose total metal content, expressed in elemental form, is greater than or equal to 0.1 µg/kg and less than or equal to 500 mg/kg is reacted with a chlorinating agent,
wherein said process further exhibits the following features:
the iron content of the glycerol is less than or equal to 100 mg/kg;
the nickel content of the glycerol is less than or equal to 10 mg/kg;
the chromium content of the glycerol is less than or equal to 10 mg/kg;
the copper content of the glycerol is less than or equal to 10 mg/kg;
the cumulative lead, arsenic and cobalt content of the glycerol is less than or equal to 5 mg/kg;
the titanium content of the glycerol is less than or equal to 10 mg/kg;
the cumulative titanium, vanadium, tin and tellurium content of the glycerol is less than or equal to 10 mg/kg;
the cumulative cadmium and antimony content of the glycerol is less than or equal to 5 mg/kg;
the mercury content of the glycerol is less than or equal to 1 mg/kg;
the zinc content of the glycerol is less than or equal to 10 mg/kg;
the cumulative selenium and zinc content of the glycerol is less than or equal to 12 mg/kg;
the cumulative sodium and calcium content of the glycerol is less than or equal to 50 mg/kg;
the aluminium content of the glycerol is less than or equal to 10 mg/kg; and
the bismuth content of glycerol is less than or equal to 5 mg/kg.

19. The process according to claim 18, wherein the total metal content of the glycerol, expressed in elemental form, is greater than or equal to 0.1 µg/kg and less than or equal to 50 mg/kg.

* * * * *